United States Patent [19]

Holst et al.

[11] 4,197,371

[45] Apr. 8, 1980

[54] WATER VAPOR ABSORBING AND TRANSMITTING SHEET MATERIAL OF RUBBER CONTAINING A SWELLABLE CROSS-LINKED CELLULOSE ETHER OR STARCH ETHER AND A PROCESS FOR THE MANUFACTURE THEREOF

[75] Inventors: Arno Holst; Walter Schermann, both of Wiesbaden; Wilhelm Fischer, Pirmasens, all of Fed. Rep. of Germany

[73] Assignee: Hoechst Aktiengesellschaft, Fed. Rep. of Germany

[21] Appl. No.: 932,620

[22] Filed: Aug. 10, 1978

[30] Foreign Application Priority Data

Aug. 11, 1977 [DE] Fed. Rep. of Germany ....... 2736205

[51] Int. Cl.² .................... B29D 27/00; C08L 1/28; C08L 3/08

[52] U.S. Cl. ...................................... 521/84; 521/65; 521/905; 521/916; 260/17 R; 260/17.4 BB; 260/17.4 ST; 260/17.4 UC

[58] Field of Search ................. 260/17.4 ST, 17.4 BB, 260/17 R; 521/65, 84, 905, 916

[56] References Cited

U.S. PATENT DOCUMENTS 3,137,664   6/1964   Shulman ...................... 260/17.4 ST Primary Examiner—Edward M. Woodberry
Attorney, Agent, or Firm—James E. Bryan

[57] ABSTRACT

This invention relates to an improvement in a sheet material comprising natural or synthetic rubber or a rubber-like polymer, which is capable of absorbing and transmitting water vapor and which contains a uniformly incorporated addition of polymer particles, the improvement that the addition comprises particles of at least one swellable modified polymer. The invention also relates to a process for the manufacture of the sheet material.

5 Claims, No Drawings

WATER VAPOR ABSORBING AND TRANSMITTING SHEET MATERIAL OF RUBBER CONTAINING A SWELLABLE CROSS-LINKED CELLULOSE ETHER OR STARCH ETHER AND A PROCESS FOR THE MANUFACTURE THEREOF

This invention relates to a sheet material of natural or synthetic rubber or of a rubber-like polymer, which has an improved water vapor absorbing and transmitting capacity, and to a process for the manufacture of this sheet material.

Sheet materials of rubber are used for various industrial purposes, for example, for the manufacture of rubber shoes, sponge rubber and cellular rubber, rubberized fabrics (e.g. for raincoats, tents or coatings for carpet backs), or dipped rubber articles (e.g. surgical gloves). Processes for the manufacture of sheet materials of this kind have been known for a long time. They are usually produced in the form of self-supporting films or multilayer sheet materials, e.g., comprising a covering layer and a support layer (see, for example, "Ullmanns Encyklopädie der technischen Chemie", Verlag Urban & Schwarzenberg, Munich 1957, Volume 9, Third Edition, headword "Kautschuk", in particular pages 351 et seq., 365 et seq., and 375 et seq., or S. Boström, "Kautschuk-Handbuch", Verlag Berliner Union, Stuttgart 1961, Volume 4, First Edition, in particular page 172 et seq. and page 263 et seq.). When these sheet materials are used under physiological conditions, for example, as coated textile material or as a shoe or in the form of a sponge (cellular) rubber for inner soles of shoes, or as upholstery covers, it is essential that the material should be capable of absorbing water vapor and, if possible, it should also be capable of transmitting water vapor to ensure, e.g., comfortable wearing.

Because the sheet materials in question are frequently used for purposes which require a water-repellent effect, and because they produce this effect at a relatively moderate price, the simultaneous disadvantage of non-absorption or non-transmission of water vapor (e.g. resulting from perspiration) is often accepted. Nevertheless, many experiments have been conducted to remedy this obvious imperfection; in particular, it has been attempted to increase the porosity of the sheet materials. However, by this measure, i.e. usually by an incorporation of additional pores in the rubber sheet materials, the structural strength of the products manufactured from these sheet materials is reduced, and in some cases the usually required impermeability to water of the products cannot be maintained. Although these foamed sheet materials transmit water vapor to a certain extent, they do not absorb water vapor to an appreciable degree.

German Pat. No. 910,960, discloses a process for the manufacture of porous, highly absorbent sheet materials. Apart from the normally formed openings, the products resulting from this process contain artificially produced fine and superfine pores and are, therefore, reported to be absorbent. The additional fine pores are produced by means of water-soluble substances which are incorporated in the sheet materials in a finely divided form during the manufacture thereof and which are dissolved out of the finished materials leaving fine pores. As pore formers water-soluble organic substances are used, for example, starch, protein or protein-like substances, sugar, tragacanth, cellulose derivatives, and synthetic resins, or substances which become water-soluble by the action of ferments or enzymes. In the manufacture of the sheet materials the base material comprising a non-woven web is treated with an impregnating agent which contains the pore former; as the impregnating agent aqueous dispersions or emulsions of vulcanizable substances, such as natural rubber, synthetic rubber or synthetic resin, may be used.

In German Auslegeschrift No. 1,204,186, a process is described for the manufacture of an absorbent, porous, coated fabric, similar to a chamois leather. In this process, a blended fabric comprising cotton and cellulose fibers is roughened down to the interior of the individual threads; then, the blended fabric is cleaned and de-sized and then the roughened fibers of the blended fabric are, on one or both sides, provided with a thin coating of a paste composed of natural or synthetic rubber latex, a substance which increases the viscosity and a readily soluble salt suitable for pore formation; and finally, the sheet material is dried and the pore former is washed out. As substances which increase the viscosity, vegetable gum, tragacanth, starch, dextranes and gum arabic are suitable, and as pore formers sodium sulfate and sodium chloride are suitable.

German Offenlegungsschrift No. 2,364,628, discloses a structure, rendered hydrophilic, of a fiber-forming and a film-forming water-insoluble polymer, which contains particles of a modified cellulose ether. The following are suitable as polymers: regenerated cellulose (cellulose hydrate), cellulose acetate, polyalkylenes, alkylcellulose, polyacrylonitrile, polyamides and polyesters. The modified cellulose ethers are such that if only etherification were carried out to the given extent, water-soluble cellulose ethers would result, but which are modified in such a way that, at least for the major part, they are water-insoluble, but retain the capacity to absorb water. The particles of modified cellulose ether may be uniformly distributed in the polymeric mass of the structure, rendered hydrophilic, or it may have a surface covering of the particles. Ion exchangers and dialysis or osmosis membranes are among the uses for films manufactured in this way.

It is an object of the invention to provide a sheet material based on rubber, which is capable of absorbing and transmitting water vapor and which is improved as compared to prior art materials.

The invention is based on a sheet material which is capable of absorbing and transmitting water vapor, comprising natural or synthetic rubber or a rubber-like polymer and containing a uniformly incorporated addition of polymer particles. In the sheet material according to the invention, the addition is composed of particles of at least one swellable modified polymer. By swellable polymers those polymers are to be understood which swell in aqueous liquids, in particular liquids containing more than 50 percent by weight of water, or which swell by the action of water molecules (e.g. water vapor) coming into contact with them in another way. The term "uniformly incorporated" denotes a random distribution. The polymer is, in particular, water-insoluble to the extent of at least about 50 percent by weight.

In a preferred embodiment, the sheet material contains the particles of at least one swellable modified polymer in an amount of about 5 to 30 percent by weight, relative to the proportion of rubber. Appropriately, the particle size is $\leq 250$ μm, particularly $\leq 150$ μm, and the particles are generally in a pulverulent or fibrous form.

The following are examples of polymers suitable as the swellable modified polymer for the additive in the material according to the invention:

A cross-linked polyalkylene oxide, for example, as described in German Offenlegungsschrift No. 2,048,721. To manufacture this product, water-soluble polyalkylene oxides are preferably treated with ionizing radiation of sufficient intensity to effect cross-linking and to render the polymer insoluble. The polyalkylene oxide can be irradiated in the solid state or in solution.

An absorbent, cross-linked copolymer containing carboxyl groups, for example, as described in German Offenlegungsschrift No. 2,507,011, and obtained from an α,β-unsaturated acid and an acetal of the general formula

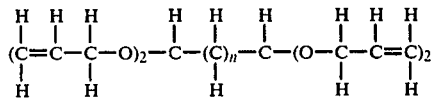

where n is 0, 1 or 2. Acrylic acid, methacrylic acid, itaconic acid, α-phenylacrylic acid or a α-benzylacrylic acid are particularly suitable as the α,β-unsaturated acid; in the manufacture of this copolymer, 0.1% to 15% by weight of the acetal are advantageously used per 85% to 99.9% by weight of an unsaturated acid.

A hydrocolloidal polymer, for example as disclosed in U.S. Pat. No. 3,670,731 (=DE-OS No. 1,642,072), which has been rendered water-insoluble by cross-linking and is suitable for absorbing liquids and also retaining them; certain polyacrylamides, alkali metal salts of hydrolyzed polyacrylamides and alkali metal salts of polystyrene sulfonic acids are especially useful.

A cross-linked, insoluble, physiologically harmless polymer which is swellable in water, for example as disclosed in U.S. Pat. No. 3,669,103 (=DE-OS No. 1,617,998) including poly-N-vinylpyrrolidones, polyacrylamides, polyacrylic acid, and polyglycols.

Absorbent polymers which are at least substantially water-insoluble and swellable with water and which have been manufactured as described in, for example, German Offenlegungsschrift No. 2,541,035; and prepared by etherification, in a homogeneous phase, of polyhydroxymethylene in an aqueous-alkaline solution with an α-halogenocarboxylic acid and by reaction, before, during or after the etherification, with a cross-linking agent which in an alkaline medium is polyfunctional towards polyhydroxymethylene.

The following swellable, modified carbohydrate derivatives are especially suitable for use in the invention: alkali metal salts of carboxymethylcellulose, which are heat-treated and are swellable in water, prepared as described, for example, in U.S. Pat. No. 2,639,239, by reducing the solubility of a water-soluble alkali metal salt of carboxymethylcellulose having a D.S. (=degree of substitution, i.e., the number of substituted hydroxyl groups on one anhydro-D-glucose unit) of 0.5 up to about 1, by subjecting the dry salt, in a finely divided form, to a temperature of about 130° C. to about 210° C., highly swellable gel particles being obtained.

Water-insoluble, heat-treated carboxyalkylcelluloses, which absorb and retain liquids, as described in, for example, U.S. Pat. No. 3,723,413 (=DE-OS No. 2,314,689); manufactured by a procedure in which (a) cellulose materials are treated with carboxyalkylating reactants to form water-soluble carboxyalkylcellulose which has an average degree of substitution of more than 0.35 carboxyalkyl radicals per anhydroglucose unit in the cellulose but which possesses poor properties with respect to the absorption and retention of liquids, (b) a proportion of the carboxyalkylating reactants and the by-products formed during the reaction is removed so that, relative to the weight of the water-soluble carboxyalkylcellulose, at least about 3% by weight thereof remain and (c) the carboxyalkylcellulose is subjected to a heat treatment in the presence of the remaining carboxyalkylating reactants and by-products of the reaction and, thus, is rendered water-insoluble, and excellent properties with respect to the absorption and retention of liquids are imparted to the carboxyalkylcellulose.

Absorbent carboxymethylcellulose fibers which are suitable for use in fiber materials for absorbing and retaining aqueous solutions and are substantially water-insoluble, as described, for example, in U.S. Pat. No. 3,589,364 (=DE-OS No. 1,912,740); fibers of this type consist of wet cross-linked fibers of water-soluble salts of carboxymethylcellulose having a D.S. of about 0.4 to 1.6 and possess the original fiber structure. Preferably, about 3 to 10 percent by weight of epichlorohydrin are employed as the cross-linking agent.

Chemically cross-linked, swellable cellulose ethers, according to U.S. Pat. No. 3,936,441 (=DE-OS No. 2,357,079); these cross-linked cellulose ethers, in particular those obtained from carboxymethylcellulose, carboxymethyl hydroxyethylcellulose, hydroxyethylcellulose or methylhydroxyethylcellulose, are manufactured by reacting the ethers, which in themselves are water-soluble, in an alkaline reaction medium with a cross-linking agent, the functional groups of which are

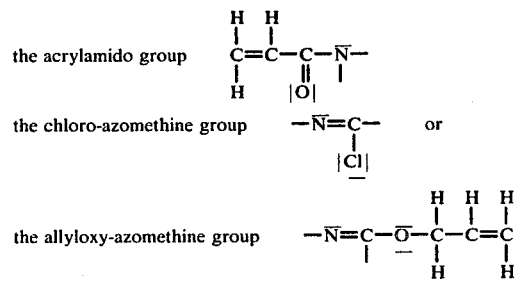

or with cross-linking agent is dichloroacetic acid or phosphorus oxychloride.

Chemically modified swellable cellulose ethers, according to U.S. Pat. No. 3,965,091 (=DE-OS No. 2,358,150); these cellulose ethers which have not been modified by cross-linking are manufactured by reacting the ethers, which in themselves are water-soluble, in an alkaline reaction medium with a monofunctionally reacting compound having one of the two formulae

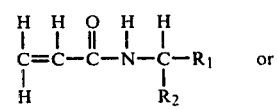 I

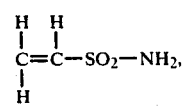 II wherein $R_1$ denotes a hydroxyl group, an acylamino group or an esterified carbamino group, and $R_2$ denotes hydrogen or a carboxyl group.

Chemically cross-linked swellable cellulose ethers, according to German Offenlegungsschrift No. 2,519,927; these cross-linked cellulose ethers are manufactured by reacting the ethers, which in themselves are water-soluble, in an alkaline reaction medium with bis-acrylamido-acetic acid as the cross-linking agent.

Free-flowing, hydrophilic carbohydrates, which are cross-linked by radiation and are swellable in water, according to German Auslegeschrift No. 2,264,027; these products are manufactured (in the case of certain polymers, such as polyethylene oxide or polyvinyl alcohol, similar products also can be obtained by the reaction steps which follow) by:

(a) mixing at least one water-soluble, pulverulent polymeric carbohydrate with such an amount of at least one pulverulent inert filler, the particles of which are smaller than those of the carbohydrate, and in such a way that a substantial part of the surface of the pulverulent carbohydrate is covered, (b) while the mixing is continued, contacting the mixture, while stirring thoroughly, with a finely divided water spray in such an amount that the mixture remains in the form of free-flowing particles and (c) then subjecting the resulting mixture to ionizing radiation until the polymeric carbohydrate is cross-linked.

Chemically cross-linked or otherwise modified swellable starch ethers, according to German Application No. P 26 34 539.1; these special starch ethers are manufactured by, for example, carrying out, as the modification, cross-linking with a cross-linking agent which is phosphorus oxychloride or which carries one of the following functional groups reactive towards hydroxyl groups:

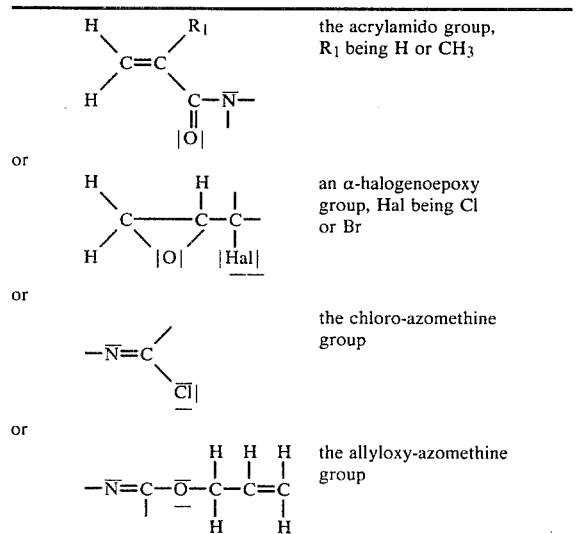

the acrylamido group, $R_1$ being H or $CH_3$ or an α-halogenoepoxy group, Hal being Cl or Br or the chloro-azomethine group or the allyloxy-azomethine group The procedure in another mode of manufacture is that the modification is carried out using a compound which is monofunctionally reactive under the stated conditions towards the hydroxyl groups of starch or of the starch ether and which is described by one of the general formulae which follow:

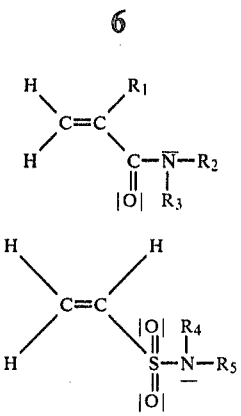

or $R_1$ being $CH_3$ or H, $R_2$ being H and $R_3$ being $CH_3$, $CH_2$—OH, a N-methylene-acylamido group with 1 to 3 carbon atoms, an esterified N-methylene-carbamido or N-carboxymethylene-carbamido group with 2 to 7 carbon atoms, or $R_2$ and $R_3$ being $CH_3$ or $CH_2$—OH and $R_4$ and $R_5$ being H, or $R_4$ being H and $R_5$ being $CH_3$, or $R_4$ and $R_5$ being $CH_3$.

Alkali metal salts of carboxymethylcellulose, having an increased absorption capacity and retention capacity, as described, for example, in U.S. Pat. No. 3,678,031 (=DE-OS No. 2,151,973). Although the etherifying agents here employed contain carboxyl groups and would lead to a normally soluble cellulose ether, the conditions of the reaction are selected so that alkali metal salts of carboxymethylcellulose, having a D.S. of 0.4 to 1.2, a water soluble fraction of <35% by weight, a water retention value (WRV) of about 1,000 to 7,000 and a salt water retention value of about 400 to about 2,500, are formed.

Water-insoluble carboxymethylcelluloses, such as are used, for example, in German Pat. No. 1,079,796 and German Auslegeschrift No. 1,151,474, i.e., those which have a D.S. of 0.05 to 0.3 and those which are substantially water-insoluble and also have a low D.S.

Water-insoluble, more highly polymerized carboxymethylcellulose or carboxyethylcellulose with a significant content of free carboxyl groups, as described, for example, in British Pat. No. 725,887 (=German Pat. No. 1,037,076), which are rendered water-insoluble by heating the water-soluble acid compounds to 80° C. to 177° C.

Phosphorylated cellulose fibers, as described, for example, in German Offenlegungsschrift No. 2,447,282, such as can be produced by a reaction of cellulose pulp with urea and phosphoric acid under the action of heat, subsequent acid hydrolysis and ultimately a conversion into the form of a salt.

Dry, solid, water-insoluble absorbents, which are swellable with water, as described, for example, in German Offenlegungsschrift No. 2,609,144, which consist of an ionic complex of a water-insoluble anionic polyelectrolyte and a cation of a metal which is at least trivalent; suitable polyelectrolytes are polyacrylic acid, starch derivatives or cellulose derivatives.

Cellulose graft polymers, as described, for example, in German Offenlegungsschrift No. 2,516,380, which are prepared by grafting side chains of ionic or non-ionic polymer radicals onto cellulose. For example, polyacrylic acid, sodium polyacrylate, polymethacrylic acid, potassium polymethacrylate, polyvinyl alcohol sulfate, polyphosphoric acid, polyvinylamine, poly-(4-vinylpyridine), hydrolyzed polyacrylonitrile, polymethyl methacrylate, polyvinyl acetate, polystyrene or polybutadiene are suitable for this purpose.

Granulated, water-insoluble alkali metal carboxylate salts of starch/acrylonitrile graft copolymers, as described, for example, in U.S. Pat. No. 3,661,815, which are manufactured by saponifying starch/acrylonitrile graft copolymers with a base in an aqueous-alkaline medium.

Modified cellulose material, having an improved retention capacity both for water and physiological fluids, as described, for example, in German Offenlegungsschrift No. 2,528,555, which is prepared by grafting an olefinically unsaturated, polymerizable monomer with hydrolyzable functional groups or a monomer carrying functional carboxyl groups onto a fibrous cellulose material and hydrolyzing the grafted product or treating the latter with alkali in other ways. In this process, the product is first converted to the state of maximum swelling, is then acidified to a pH value at which it is in the state of minimum swelling, is then converted to the form of a salt under conditions which do not effect swelling and is finally dried.

Modified polysaccharide, as described, for example, in German Offenlegungsschrift No. 2,647,420, manufactured from a polysaccharide, acrylamide, another vinyl monomer and a divinyl monomer, under the conditions of a free-radical reaction.

Processes for the manufacture of sheet materials from rubber are known. The sheet material may be a self-supporting film or it may be produced by coating or impregnating a base of natural or synthetic fiber material, non-woven textile materials or webs of synthetic resin; the rubber proportion may be present in solid or foamed form. For coating or impregnating the following bases are preferably used:

Woven or non-woven textile materials having one or more components, for example of synthetic fibers, such as polyamides, polyesters, polyacrylonitrile, PVC, polyolefins and polyamino acids, and also of glass fibers, regenerated fibers, such as viscose or acetate fibers, of natural fibers, such as cotton, silk, wool, linen and collagen obtained by abrading natural leather; or sheets of one or more components, for example of synthetic resin, such as polyamides, polyesters, polyacrylonitrile, PVC, polyolefins and polyamino acids, or of natural leather from which the silvery surface has been removed, or of collagen obtained from waste leather, natural rubber and synthetic rubber.

The bases may be coated or impregnated using various methods; similarly various methods may be employed for the manufacture of self-supporting films. Rubber is the base material in the manufacture of the sheets according to the invention. By the generic term "rubber" the following are, for example, to be understood: latex of wild or cultivated rubber, pre-vulcanized latex, positex (latex the negative charge of which has been converted into a positive charge), dispersions of rubber and reclaimed rubber, raw rubber types such as "smoked sheets" and "crepe", synthetic rubber types, such as copolymers of butadiene and styrene and of butadiene and acrylonitrile, polymers and copolymers of chlorobutadiene, polymers and transformed polymers comprising vinyl compounds, copolymers of isobutylene and isoprene, block polymers of butadiene, thioplasts, silicone rubber, reclaimed rubber, Factice and others.

Generally, the rubber can be processed as follows:

In the case of latex, the vulcanizing agents and other auxiliaries, for example, filler, age resister, plasticizer, etc., are first stirred up with the latex, and then the desired sheet material may be produced, for example, according to the dip tank method with or without coagulating agents, according to the foaming method, by electrophoretic deposition, according to the impregnating method or by spreading.

In the case of solid rubber, the raw rubber bales are first broken up, the rubber is plasticized and the mixture to be processed is produced using conventional auxiliaries; the desired sheet material then may be prepared, for example, by calendering, frictioning and dipping or spreading of rubber solutions; finally, the rubber film of the rubber-containing layer is vulcanized.

When carrying out the examples, the procedures described below were used (parts are given as parts by weight, percentages as percent by weight):

1. A rubber for coating textile material is prepared by producing the below-specified vulcanizable mixture on a roll and dissolving 30 parts of this mixture in 70 parts of a gasoline/toluene mixture comprising 60 parts of gasoline and 10 parts of toluene.
   60.0% of smoked sheets
   10.0% of Factice
   20.0% of soot
   6.0% of zinc oxide
   1.5% of sulfur
   1.0% of a vulcanizing accelerator
   1.0% of an antioxidant
   0.5% of stearic acid.

Prior to spreading or processing the solution in another way the particles of at least one modified swellable polymer are added and are uniformly distributed in the solution, the resulting mixture is then spread or shaped in another way, and finally it is vulcanized during about 30 minutes at a temperature of about 120° C.

2. A foam rubber is prepared from:
   100.0 parts of crepe
   10.0 parts of zinc oxide
   60.0 parts of chalk as a filler
   15.0 parts of mineral oil
   2.0 parts of paraffin
   3.0 parts of stearic acid
   1.0 part of a mould release agent
   3.5 parts of sulfur
   1.5 parts of a vulcanizing accelerator
   1.0 part of an antioxidant
   5.5 parts of an expanding agent in the form of a paste Prior to foaming and vulcanizing, the particles of at least one modified swellable polymer are added to this mixture and are uniformly distributed therein.

3. Based on natural latex or synthetic latex, foamed articles may be produced as described below. In this process, the particles of at least one modified swellable polymer are suspended in an amount of water corresponding to about four times the amount of particles, they are added to the latex mixture prior to expanding, coagulating and vulcanizing and are uniformly distributed therein.

3.1. The mixture comprising natural latex is composed of:
   167.0 parts of a 60 percent natural latex
   3.5 parts of a 20 percent aqueous sodium stearate solution
   3.0 parts of a 10 percent aqueous solution of a dispersing agent
   2.5 parts of sulfur 1.6 parts of a vulcanizing accelerator
7.8 parts of a 5 percent aqueous emulsifier solution
2.5 parts of zinc oxide
0.8 part of an antioxidant
4.0 parts of a thickener
3.0 parts of a 15 percent aqueous solution of a foam stabilizer
For coagulating
20.0 parts of a 10 percent aqueous ammonium chloride solution are added to the above mixture.
3.2. The mixture comprising synthetic latex is composed of:
74.0 parts of buna latex
2.2 parts of K-oleate
9.0 parts of a vulcanizing paste
5.0 parts of methyl cellulose
For coagulating
2.0 to 4.0 parts of a silicofluoride
are added to the above mixture.

When manufacturing sheet materials according to the invention the particles of at least one modified swellable polymer, preferably in a proportion of 5 to 30 percent by weight, relative to the final film or layer or to the proportion of rubber in the layer are added to the base materials to be processed and are uniformly distributed therein, prior to spreading or shaping the material in another way.

The sheet materials according to the invention exhibit an excellent capability of absorbing and transmitting water vapor, which by far exceeds a mere transport effect of the incorporated particles. In addition, the sheet materials can release the absorbed water vapor again under certain conditions, for example, when transported to different climatic conditions.

The specified properties of the sheet materials depend not only upon the clearly demonstrable effect produced by the addition of the particles of at least one swellable modified polymer, but, among others, also upon the thickness of the film or the coating, respectively; therefore, the film or coating is appropriately prepared in a thickness from about 0.05 to about 0.5 mm, in particular, if a good transmission of water vapor is to be obtained, in addition to a good absorption of water vapor.

The sheet materials according to the invention having the specified properties are, for example, suitable for use as self-supporting films or as coatings on support materials, in particular as rubberized textiles, shoe uppers or insoles or materials for carpet backs, i.e., they may be used for purposes in which, under physiological conditions, body fluids, e.g., perspiration, occur. In a foamed form they also may be used as absorbents for hygienic purposes, e.g., for tampons, because the foamed material is capable of absorbing and retaining water.

The abbreviations and terms used in the description and in the examples for describing the sheet materials according to the invention and the swellable modified polymers present therein are defined as follows:

WRV—Water retention capacity of the swellable modified polymer in % by weight, measured against 2,000 times the acceleration due to gravity, relative to its water-insoluble fraction; WRV is determined after immersing the sample in water.

WUA—Water-insoluble fraction in the swellable modified polymer.

DS—Degree of substitution, i.e. the number of substituted hydroxyl groups on the anhydro-D-glucose units, from 0.0 to 3.0.

SV—Absorbency of the swellable modified polymer for a 1% NaCl solution in percent by weight, relative to its total weight; SV is determined after a 1% aqueous NaCl solution has been absorbed by the sample up to saturation.

$WDA_{DIN}$—The water vapor absorption is determined as the weight loss of a sample dried to constant weight, relative to the original weight under the conditions according to DIN 53 304 (May 1968 Edition) at 102° C.±2° C. In this method, the sample is first weighed to an accuracy of ±0.001 g, immediately after it has been taken out of a water vapor-tight container. The samples are then dried suspended in a heating cabinet at a temperature of 102° C.±2° C. during 15 hours; following cooling to room temperature they are again weighed to an accuracy of ±0.001 g. In order to be able thoroughly to test the water-vapor absorption of the samples under different conditions, the particular samples are suspended in different climatic conditions and after certain time intervals they are taken out and their absorption of water vapor is determined in percent by weight, relative to their initial weight at the start of the particular measurement.

$WDD_{PFI}$—Water vapor transmission rate (in accordance with W. Fischer and W. Schmidt, "Das Leder", E. Roether-Verlag, Darmstadt, 27, 87 et seq. (1976)). The interior of the apparatus is maintained at 32° C., and the sample (which forms a "window" to the apparatus) is under standard climatic conditions—unless otherwise stated—of 23° C./50% relative humidity, these conditions being kept constant by means of a gentle stream of air from a fan mounted above the apparatus. The free test surface has an area of 10 cm². Inside the apparatus, the water at 32° C. and the atmosphere above the water, which is saturated with water vapor, are kept in continuous motion with the aid of a magnetic stirrer. To determine the WDD, the weight loss of the test vessel with the sample is determined. WDD is expressed in mg/cm²·x hours (in most cases x is 1, but it also can be 8 or 24).

$WDA_{PFI}$—Water vapor absorption (see also $WDD_{PFI}$). The water vapor absorption is determined simultaneously with the measurement of $WDD_{PFI}$, by determining the increase in weight of the sample; unless otherwise stated, the sample is permeable with respect to the outside climatic conditions, i.e., it is not covered.

In all of the examples which follow, the representative modified swellable polymers used are sodium carboxy methyl cellulose which are chemically crosslinked with bisacrylamido acetic acid and which have the following parameters: WUA≧ 70%, WRV=400 to 700%, SV=800 to 1,400%, DS=0.8 to 1.1 and a particle size of ≦200 μm with a proportion of 90 percent by weight of ≦100 μm.

EXAMPLES 1 TO 3 AND COMPARATIVE EXAMPLE V 1 (TABLE I)

According to the invention a rubber-coated cotton fabric is prepared containing an addition of a modified swellable polymer in various proportions in the rubber layer (15% by weight in Example 1, 20% by weight in Example 2 and 25% by weight in Example 3, relative to the weight of the layer). This material is compared with a rubber-coated fabric without addition (V 1), in view of the transmission and absorption of water vapor. The measured values increase with an increasing proportion of the modified swellable polymer; the tests carried out do not reveal a significant influence on the mechanical properties of the coated fabric. As compared with the coated fabrics without addition, the coated fabrics with an addition according to the invention show a clear transmission and absorption of water vapor.

EXAMPLES 4 TO 6 AND COMPARATIVE EXAMPLES V 2 TO V 4 (TABLE II)

According to the invention a foam rubber (in various thicknesses) is prepared from a rubber mass containing an addition of a modified swellable polymer in a proportion of 15% by weight, relative to the weight of the foam rubber. This material is compared with a foam rubber of the same thickness without addition, with a view to the increasing absorption of water vapor following an increasing duration of the action of the water vapor.

The foam rubbers have the following structures:

Examples V2 and Example 4: the two outside surfaces are covered by a rubber skin Example V 3 and Example 5: one outside surface shows an open-cell foam and the other outside surface is covered by a rubber skin Example V4 and Example 6: the two outside surfaces show an open-cell foam A foam rubber with an addition prepared according to the invention absorbs a higher amount of water vapor than a similar foam rubber without addition.

EXAMPLE 7 AND COMPARATIVE EXAMPLE V 5 (TABLE III)

According to the invention a foam is prepared from natural latex containing an addition of 15% by weight of a modified swellable polymer, relative to the weight of the final latex foam (Example 7). This material is compared with a latex foam without addition (V 5), with a view to the absorption of water vapor in different climatic conditions and in the case of an increasing duration of the action of the water vapor. A latex foam prepared according to the invention absorbs a considerably higher amount of water vapor than a similar foam without addition.

EXAMPLES 8 TO 10 AND COMPARATIVE EXAMPLE V 6 (TABLE IV)

According to the invention a foam is prepared from synthetic latex containing various proportions of an addition (10% by weight in Example 8, 20% by weight in Example 9, and 30% by weight in Example 10, relative to the weight of the final latex foam). The water vapor absorption of this material is compared with the water vapor absorption of a latex foam without addition (V 6). The foam materials are exposed to an atmosphere of 65% relative humidity (r.F.) at a temperature of 20° C. and subsequently to various moist atmospheres, and the respective increase or decrease of humidity is measured after certain time intervals. An increasing amount of addition is accompanied by an increase in the water vapor absorption of the foam. A foam containing the addition absorbs a considerably higher amount of water vapor than a similar foam without addition.

TABLE I

| Example | Thickness of Test Specimen (mm) | WDD in PFI | | WDA in PFI | |
|---|---|---|---|---|---|
| | | mg/cm$^2$ . 8h | mg/cm$^2$ . h | mg/cm$^2$ . 8h | % by weight |
| VI | rubber layer 0.2 woven fabric layer 0.4 | 0.55 | 0.07 | 0.60 | 0.44 |
| 1 | | 2.79 | 0.35 | 3.03 | 2.61 |
| 2 | woven fabric layer 0.4 | 2.83 | 0.35 | 11.87 | 10.85 |
| 3 | woven fabric layer 0.4 | 20.50 | 2.56 | 19.59 | 23.57 |

TABLE II

| Example | Thickness of Test Specimen (mm) | Dimensions of Test Specimen (mm$^2$) | Increase of WDA$_{DIN}$ in % by weight after* | | | | | |
|---|---|---|---|---|---|---|---|---|
| | | | 1h | 2h | 4h | 8h | 12h | 24h |
| V2 | 25 | 50 × 100 | 0.03 | 0.05 | 0.07 | 0.12 | 0.16 | 0.25 |
| 4 | 25 | " | 0.11 | 0.17 | 0.27 | 0.45 | 0.61 | 0.95 |
| V3 | 5 | " | 0.10 | 0.14 | 0.23 | 0.37 | 0.50 | 0.82 |
| 5 | 5 | " | 0.46 | 0.68 | 0.99 | 1.50 | 1.90 | 3.01 |
| V4 | 20 | " | 0.04 | 0.05 | 0.08 | 0.13 | 0.16 | 0.26 |
| 6 | 20 | " | 0.44 | 0.62 | 1.00 | 1.54 | 2.01 | 3.13 |

*The test specimens were removed from climatic conditions of 20° C. and 65% relative humidity and were stored at 20° C. and 95% relative humidity.

TABLE III

| Example | Thickness of Test Specimen (mm) | Dimensions of Test Specimen (mm$^2$) | Duration of Measurement (h) | WDA$_{DIN}$ in % by weight under climatic conditions of | | | |
|---|---|---|---|---|---|---|---|
| | | | | 20° C./20% r.F. | 20° C./35% r.F. | 20° C./65% r.F. | 20° C./95% r.F.* |
| V5 | 5.5 | 50 × 100 | 4 | 0.01 | 0.03 | 0.04 | 0.45 |
| | | | 8 | 0.01 | 0.03 | 0.07 | 0.50 |
| | | | 12 | 0.01 | 0.04 | 0.08 | 0.88 |
| 7 | 5.5 | 50 × 100 | 4 | 0.80 | 1.20 | 1.92 | 7.22 |

TABLE III-continued

| Example | Thickness of Test Specimen (mm) | Dimensions of Test Specimen (mm$^2$) | Duration of Measurement (h) | WDA$_{DIN}$ in % by weight under climatic conditions of | | | |
|---|---|---|---|---|---|---|---|
| | | | | 20° C./20% r.F. | 20° C./35% r.F. | 20° C./65% r.F. | 20° C./95% r.F.* |
| | | | 8 | 0.89 | 1.24 | 2.38 | 9.32 |
| | | | 12 | 0.94 | 1.28 | 2.41 | 10.83 |

*r.F. = relative humidity

TABLE IV

| Example | Thickness of Test Specimen (mm) | Dimensions of Test Specimen (mm$^2$) | Duration of Measurement (h) | Increase or Decrease (% by weight) of WDA$_{DIN}$* at | | |
|---|---|---|---|---|---|---|
| | | | | 20° C./20% r.F. | 20° C./35% r.F. | 20° C./95% r.F. |
| V6 | 5.5 | 50 × 100 | 4 | −0.06 | −0.03 | +0.39 |
| | | | 8 | −0.06 | −0.03 | +0.46 |
| | | | 24 | −0.06 | −0.03 | +0.80 |
| 8 | 5.5 | 50 × 100 | 4 | −0.48 | −0.13 | +3.30 |
| | | | 8 | −0.51 | −0.36 | +3.81 |
| | | | 24 | −0.53 | −0.36 | +6.35 |
| 9 | 5.5 | 50 × 100 | 4 | −1.31 | −0.96 | +6.51 |
| | | | 8 | −1.36 | −1.00 | +7.96 |
| | | | 24 | −1.40 | −1.03 | +13.51 |
| 10 | 5.5 | 50 × 100 | 4 | −1.98 | −1.47 | +7.84 |
| | | | 8 | −1.99 | −1.52 | +12.17 |
| | | | 24 | −2.12 | −1.57 | +18.21 |

*All values are related to the initial WDA$_{DIN}$ under climatic conditions of 20° C. and relative humidity (r.F.)

It will be obvious to those skilled in the art that many modifications may be made within the scope of the present invention without departing from the spirit thereof, and the invention includes all such modifications.

What is claimed is:

1. In a sheet material comprising natural or synthetic rubber or a rubber-like polymer, which is capable of absorbing and transmitting water vapor and which contains a uniformly incorporated addition of polymer particles, the improvement comprising that the addition comprises particles of at least one swellable modified starch either or cellulose ether, which is modified by cross-linking effected by heat energy, or radiation, or by an additional chemical compound, which is insoluble in water to the extent of at least about 50 percent by weight, and which swells in aqueous liquids.

2. A sheet material according to claim 1 in which the addition amounts to about 5 to 30 percent by weight, relative to the rubber proportion.

3. A process for the manufacture of a water vapor-absorbing and transmitting sheet material comprising (a) adding particles of at least one swellable modified starch ether or cellulose ether, which is modified by cross-linking effected by heat energy, or radiation, or by an additional chemical compound, which is insoluble in water to the extent of at least about 50 percent by weight, and which swells in aqueous liquids, to a rubber-containing base material, (b) uniformly distributing the particles therein, (c) spreading the mixture, and (d) stabilizing it.

4. A process according to claim 3 in which the mixture is spread with simultaneous foaming.

5. A process according to claim 3 in which the particles are added in a proportion of 5 to 30 percent by weight, relative to the rubber proportion of the final sheet material.

* * * * *